United States Patent
Helmus

(10) Patent No.: US 7,108,685 B2
(45) Date of Patent: Sep. 19, 2006

(54) PATCH STABILIZATION OF RODS FOR TREATMENT OF CARDIAC MUSCLE

(75) Inventor: Michael N. Helmus, Worcester, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/121,618

(22) Filed: Apr. 15, 2002

(65) Prior Publication Data

US 2003/0195527 A1    Oct. 16, 2003

(51) Int. Cl.
*A61K 9/22* (2006.01)

(52) U.S. Cl. .................................... 604/891.1

(58) Field of Classification Search .......... 604/891.1, 604/521, 60, 9–8.502, 294, 67, 131, 890.1; 606/139, 213; 600/431, 374, 375; 607/120, 607/122, 126, 128, 129, 130; 623/2.11; 424/422, 424/423, 434
See application file for complete search history.

(56) References Cited

U.S. PATENT DOCUMENTS

| | | | | |
|---|---|---|---|---|
| 4,821,723 A | * | 4/1989 | Baker et al. ................... | 607/7 |
| 5,192,301 A | * | 3/1993 | Kamiya et al. ............. | 606/213 |
| 5,247,945 A | * | 9/1993 | Heinze et al. .............. | 607/129 |
| 5,300,110 A | * | 4/1994 | Latterell et al. ............ | 607/130 |
| 5,551,427 A | * | 9/1996 | Altman ........................ | 600/374 |
| 5,810,836 A | | 9/1998 | Hussein et al. | |
| 5,830,173 A | * | 11/1998 | Avery et al. ................... | 604/9 |
| 6,045,565 A | | 4/2000 | Ellis et al. | |
| 6,120,520 A | | 9/2000 | Saadat et al. | |
| 6,224,566 B1 | | 5/2001 | Loeb | |
| 6,726,920 B1 | * | 4/2004 | Theeuwes et al. .......... | 424/423 |
| 2002/0026176 A1 | * | 2/2002 | Varner et al. ............ | 604/891.1 |
| 2002/0177772 A1 | * | 11/2002 | Altman et al. ............. | 600/431 |
| 2003/0073972 A1 | * | 4/2003 | Rosenman et al. ......... | 604/502 |
| 2004/0204672 A1 | * | 10/2004 | Palasis et al. ................ | 604/57 |

FOREIGN PATENT DOCUMENTS

| | | |
|---|---|---|
| WO | WO 00/35376 | 6/2000 |
| WO | WO 00/54661 A1 | 9/2000 |

OTHER PUBLICATIONS

D. W. Losordo, et al., "Gene Therapy for Myocardial Angiogenesis Initial Clinical Results With Direct Myocardial Injection of phVEGFG$_{165}$ as Sole Therapy for Myocardial Ischemia", 98 Circulation 2785, 2800-04 (Dec. 22, 1998).
http://www.bioheartinc.com, 19 pages.
"Advanced Tissue Sciences Receives $2 Million NIST Award For Tissue-Engineered Ischemic Repair Device", Oct. 4, 2000, News Release, http://www.advancedtissue.com, 3 pages.

* cited by examiner

*Primary Examiner*—Sharon Kennedy
(74) *Attorney, Agent, or Firm*—Kenyon & Kenyon LLP

(57) ABSTRACT

The present invention relates to a system and method for the delivery of therapeutic agents, such as therapeutic drugs or genetic material, into the muscle or tissue that minimizes the loss of therapeutic agents due to contraction of the muscle. In one embodiment, an implant for delivering therapeutic agents into a muscle is provided, wherein the implant has at least one rod for insertion and delivery of therapeutic agents into the muscle and a patch that can be attached to the exterior surface of the muscle for preventing or minimizing therapeutic agent being expelled due to the contraction of the muscle, such as the beating of a heart muscle.

21 Claims, 6 Drawing Sheets

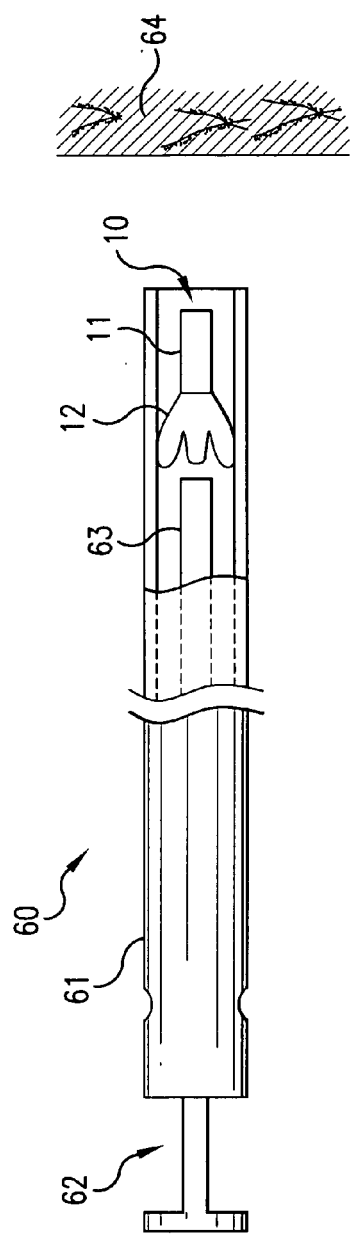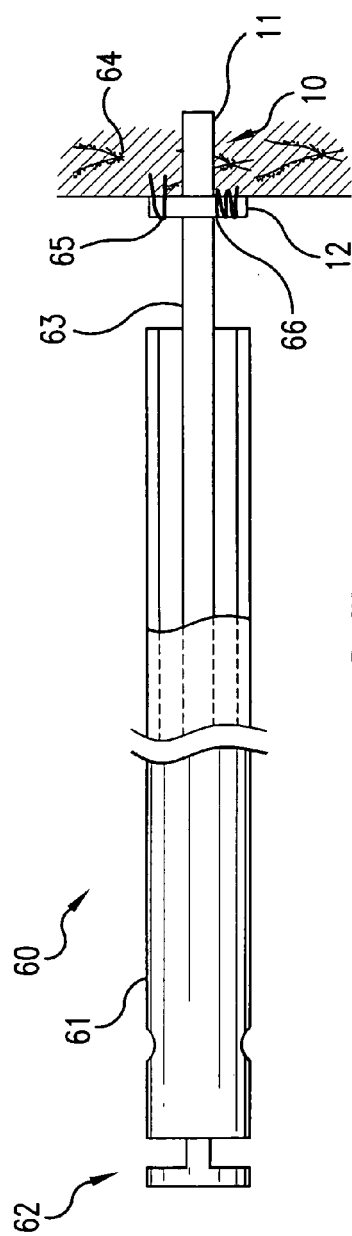
FIG.6
FIG.7

PATCH STABILIZATION OF RODS FOR TREATMENT OF CARDIAC MUSCLE

TECHNICAL FIELD

The present invention regards delivery of therapeutic agents, such as therapeutic drugs or genetic material, into a muscle or other tissue.

BACKGROUND

The delivery of therapeutic agents to diseased muscle or other tissue is an important, often repeated, procedure in the practice of modem medicine. Therapeutic agents, including therapeutic drugs and genetic material, may be used to treat, regenerate, or otherwise affect the muscle surface or the interior of the muscle itself. Such therapy can promote revascularization and create new formation of muscle, such as the myocardium of the heart. For example, many of the treatments for congestive heart failure entail the delivery of therapeutic agents, growth factors, nucleic acids, gene transfection agents, or cellular transplants, e.g. fetal cardiomyocytes, allogeneic cardiomyocytes, allogeneic or autologous myocytes, and other potentially pluripotential cells from autologous or allogeneic bone marrow or stem cells.

Current methods for delivering therapeutic agents to muscle, such as the heart muscle, entail injecting directly into the muscle a genetic cell or therapeutic drug. Delivery of therapeutic agents has been proposed or achieved using medical devices such as catheters, needle devices and various coated implantable devices such as stents. The cells and agents can be injected directly or can be formulated into gels, sealants, or microparticles for injection.

Examples of methods for delivering drugs are shown, among others, in U.S. Pat. Nos. 6,224,566, to Loeb; 6,045,565, to Ellis et al.; 6,120,520, to Saadat et al.; and PCT Publication No. WO 00/54661, to Saadat.

Certain tissue, such as heart muscle tissue, present particular difficulties for effective implantation of therapeutic agents due to the nature of the tissue. For example, the beating of a heart and contraction of the heart muscle will move and generally expel material that is inserted or injected into the heart muscle on the next compression of the heart, or over time. Thus, it is difficult to keep the therapeutic agents in the injected location for treatment, and the overall efficacy of the therapy is reduced.

When therapeutic agents injected or delivered into the muscle are expelled due to the contractions of the muscle, other problems also arise. For example, therapeutic drugs may flow directly into the bloodstream, which is potentially harmful due to the toxic nature of some therapeutic drugs. Also, the costs involved in preparing therapeutic and genetic material are high. Accordingly, any loss of therapeutic agent during treatment represents a considerable financial loss.

Accordingly, there is a need for a system that stabilizes the therapeutic agent within the muscle.

SUMMARY OF THE INVENTION

The present invention regards a system and method for the delivery of therapeutic agent, such as therapeutic drugs or genetic material, into a muscle or tissue, wherein the system minimizes the loss of the therapeutic agents due to contraction of the muscle. In one embodiment, an implant for delivering therapeutic agent into a muscle that minimizes the loss of therapeutic agent is provided, wherein the implant has at least one rod for insertion into the muscle and a patch that can be attached to the exterior surface of the muscle. The rod or rods allow delivery of the therapeutic agent into the muscle tissue, while the patch prevents the rod or rods from being forced out of the muscle tissue. The patch may also be used to deliver therapeutic agent, allowing therapeutic agents to be administered to the interior and the surface of a muscle.

In a further embodiment of the present invention, another system for delivering therapeutic agent into a muscle that minimizes the loss of therapeutic agent due to the contraction of the muscle is provided, wherein the implant has at least one rod for insertion into the muscle and a patch attached to the rod, wherein the patch can be attached to the exterior surface of the muscle after the rod is inserted.

In a further embodiment of the present invention, another system for delivering therapeutic agent into a muscle that minimizes the loss of therapeutic agent due to the contraction of the muscle is provided, wherein the system has at least one hollow rod for insertion into the muscle and a patch attached to the hollow rod, wherein the rod can be refilled with therapeutic agent through an access port mounted on the patch.

In a further embodiment of the present invention, a method for delivering therapeutic agent into a muscle that minimizes the loss of therapeutic agent due to the contraction of the muscle is provided, wherein the method includes positioning at least one rod containing a therapeutic agent adjacent a treatment site of a muscle within the patient, applying a force upon the first end of the rod thereby urging the rod through the exterior surface of the muscle and into the muscle of a patient at the treatment site; and attaching a patch onto the exterior surface of the muscle to secure the rod within the muscle to deliver a controlled amount of a therapeutic agent at the treatment site of the muscle.

In an alternative embodiment of the present invention, a method for delivering therapeutic agent into a muscle that minimizes the loss of therapeutic agent due to the contraction of the muscle is provided, wherein the method includes positioning a catheter adapted for injecting a therapeutic agent into a muscle adjacent a treatment site of a muscle within the patient; injecting the therapeutic agent into the muscle at the treatment site; positioning a patch adjacent the treatment site of the muscle; and attaching the patch onto the exterior surface of the muscle to secure the therapeutic agent within the muscle.

BRIEF DESCRIPTION OF THE DRAWINGS

FIG. 6 is an enlarged longitudinal cutaway view of an embodiment of a system for treating a muscle with a therapeutic agent in accordance with the present invention.

FIG. 7 is an enlarged longitudinal cutaway view of the system of FIG. 6 illustrating the system urged into the muscle of the patient.

DETAILED DESCRIPTION

Figure 1:
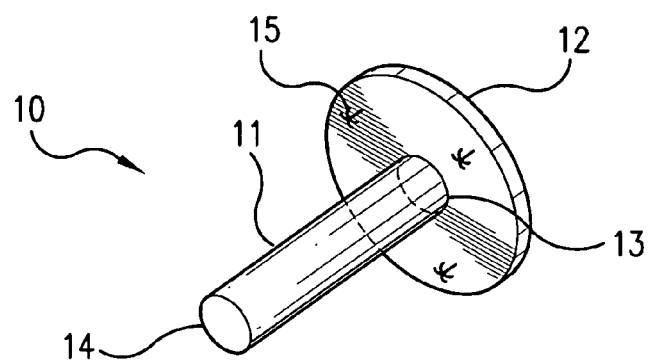
FIG. 1 is a perspective view of a therapeutic agent delivery implant in accordance with the present invention.

In FIG. 1, an implant in accordance with the present invention for delivering therapeutic agents into a muscle that minimizes the loss of therapeutic agent due to the contraction of the muscle is shown and generally designated as 10. As seen in FIG. 1, the implant 10 includes at least one rod 11 for insertion and delivery of therapeutic agent into the muscle and a patch 12. Rod 11, having a first end 13 and a second end 14, contains for example a therapeutic drug for delivery into the muscle upon insertion into a treatment site of the muscle. When the rod 11 is inserted into the muscle, therapeutic drug delivery may be initiated.

After insertion of the rod 11, patch 12 is attached to the exterior surface of the muscle to minimize or preclude the loss of therapeutic agent as the muscle contracts, such as in the beating of a heart. Thus, stability and long term delivery of the therapeutic agent can be obtained if the patch 12 is mounted to rod 11 at the first end 13 of rod 11. A person skilled in the art would appreciate that the patch 12 can be mounted on rod 11 in any manner well known in the pertinent art, such as by bonding or other mechanical attachment means. Alternatively, rod 11 and patch 12 may be separate components, wherein the patch 12 is attached to the surface of the muscle after the rod is inserted.

One skilled in the pertinent art would appreciate that the patch can be secured to the surface of the muscle in a variety of methods. For example, the patch 12 can be stabilized to the heart surface by sewing or stapling the patch 12 to the heart. Alternatively, tissue adhesives, e.g. cyanoacrylates, fibrin sealant, albumin sealants, PEG sealants, or collagen/gelatin sealants, can be used to keep the rod 11 in place for the duration of the delivery. Also, a skilled artisan would appreciate that barbs may be used to attach patch 12 to the muscle surface. Barbs 15, illustratively shown in FIG. 1, can be mounted to the surface of patch 12 that contacts the muscle surface. Thus, at least sutures, staples, adhesives, and barbs may be used as means for (fixedly) attaching the patch onto tissue (such as heart tissue) to secure the rod within the tissue as described herein. A layer of adhesive 16 is illustratively depicted in FIG. 2. Sutures 66 and staples 65 are illustratively depicted in FIG. 7.

Therapeutic agents and genetic material contained in rod 11 may be used to treat, regenerate, or otherwise affect the muscle surface or the interior of the muscle itself. For example, many of the treatments for a failing heart due to congestive heart failure entail the delivery of therapeutic agents, growth factors, nucleic acids, gene transfection agents, or cellular transplants, e.g. fetal cardiomyocytes, allogeneic cardiomyocytes, allogeneic or autologous myocytes, and other potentially pluripotential cells from autologous or allogeneic bone marrow or stem cells. The treated muscle may be any muscle located within the body of a patient. It may include chambers of the heart and any other muscle as apparent to one of skill in the art. Organs and tissues that may be treated by the methods of the present invention include any mammalian tissue or organ, whether located in vivo or ex vivo. Non-limiting examples include the heart, the lungs, the brain, the liver, the kidneys, the bladder, the intestines, the stomach, the pancreas, the ovaries, the prostate, the eyes, as well as tumors, cartilage and bone.

A plurality of rods 11 may be used in implant 10. The rods 11 can be degradable or non-degradable as well as porous or non-porous. Porous rods would allow tissue ingrowth and stabilize the rod. Further, porous rods can be utilized as cell scaffolds. The rods may be constructed from polymers or hollow metallic wire fibers. The rods may also be solid polymers infused with therapeutic agents.

A person skilled in the pertinent art would appreciate that the patch material may include any biostable biocompatible patch material, e.g. polypropylene meshes, metal alloy meshes, titanium metal alloy meshes, and solid metal or polymer disks of material. The patch can also be constructed of materials that have traditionally been used to patch septal defects and aneurysms of the heart, e.g. bovine or equine aldehyde fixed pericardium, polyester and polytetrafluorethylene fabrics, or expanded polytetrafluorethylene (ePTFE). Solid disks of material, e.g. a nonporous disk of plastic or polymer, may allow for attachment of the patch to the muscle surface through suturing or stapling. Nonporous solid disks can have holes used for attaching the patch. Porous disks may allow attachment of the patch with tissue adhesives.

Patches may be made of biodegradable materials so that the patch biodegrades once the functional life of the rod is fulfilled, i.e. the release of active agents or drugs is complete. There are a large number of biodegradable materials, including polylactic acid and its copolymers, polygalactic acid and its copolymers, polyhydroxybutarates, or polycaprolactone. One skilled in the pertinent arts would know that any other biodegradable material that can be made into a patch and can maintain its integrity after the functional life of the rod is met will be sufficient. If a biodegradable patch is utilized, it would be preferable that the rod be biodegradable and that the rod degrades prior to biodegradation of the patch.

The patch 12 shown in FIG. 1 is exemplary. One skilled in the art would appreciate that a variety of patch configurations can be designed to accommodate the variety of treated areas and the variety of rod configurations. The patch 12 can be increased or elongated and the shape can be any suitable shape, such as substantially square or substantially round.

Figure 2:
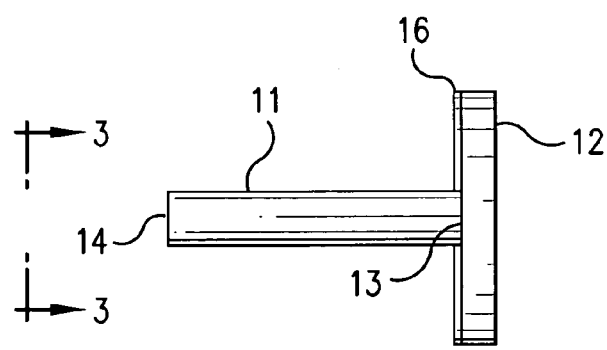
FIG. 2 is a side view of the implant of FIG. 1.
Figure 3:
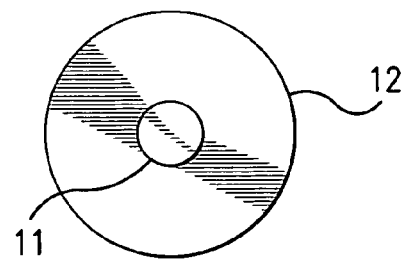
FIG. 3 is an end view of the implant of FIG. 1 taken along line 3—3 of FIG. 2.

FIG. 2 is a side view of the implant of FIG. 1. FIG. 3 is an end view of the same implant taken along line 3—3 of FIG. 2.

Figure 4:
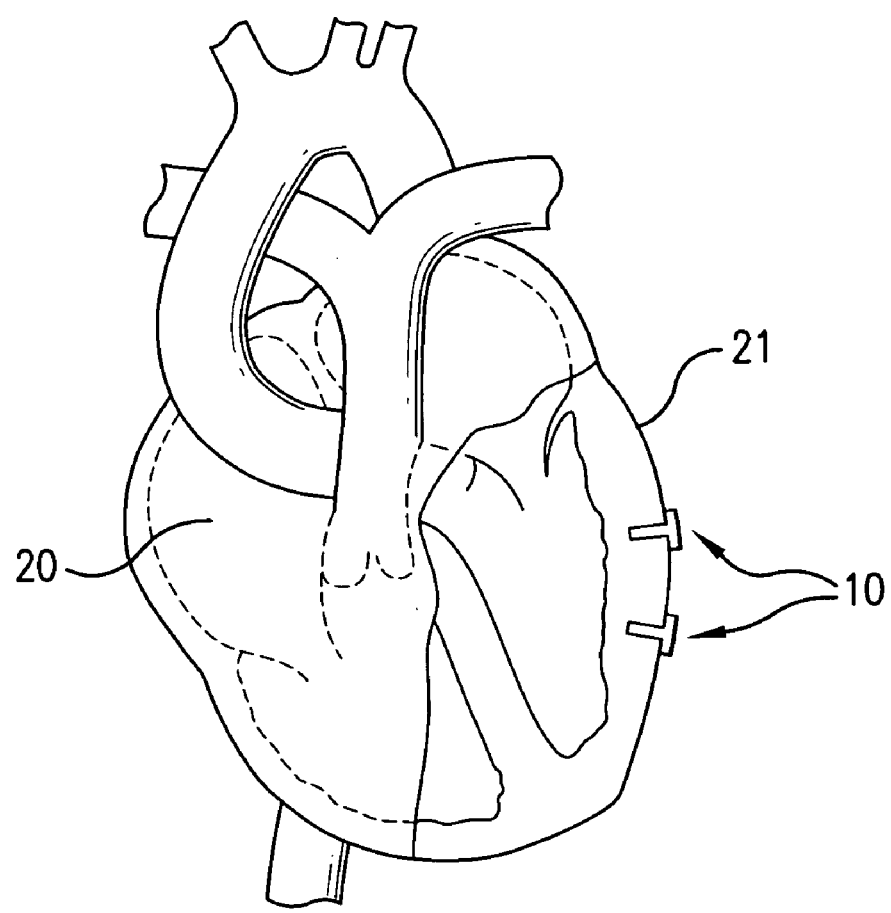
FIG. 4 is a perspective, cutaway view of a human heart having an implant in accordance with the present invention inserted into the epicardium of the heart for delivery of therapeutic agent into the muscle.
Figure 5:
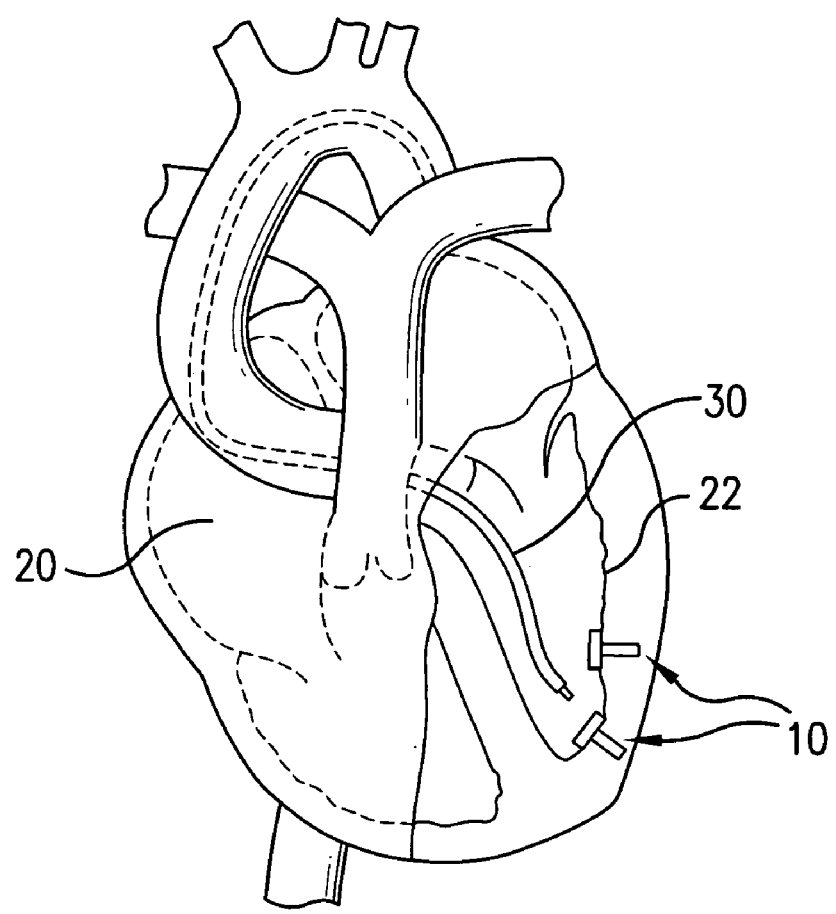
FIG. 5 is a perspective, cutaway view of a human heart having a therapeutic agent delivery catheter positioned within the heart, and showing an implant in accordance with the present invention inserted into the endocardium of the heart for delivery of therapeutic agent into the muscle.

FIG. 4 shows a perspective, cutaway view of a human heart 20 having an implant 10 in accordance with the present invention inserted into the epicardium 21 of the heart for delivery of therapeutic agent into the muscle. FIG. 5 is also a perspective, cutaway view of a human heart 20 illustrating a therapeutic agent delivery catheter 30 positioned within the heart, and showing the implant 10 inserted into the endocardium 22 of the heart 20 for delivery of therapeutic agent into the muscle. As depicted in FIG. 5, implant 10 may be inserted into the endocardium 22, or interior muscle of the heart, through an inter-luminal catheter introduced into the arteries leading to the heart. Alternatively, as shown in FIG. 4, implant 10 may be inserted into the epicardium 21, or exterior muscle of the heart, through a thoracotomy procedure or open heart surgery.

Referring to FIG. 6, a system in accordance with the present invention for delivering therapeutic agent into a muscle that minimizes the loss of therapeutic agent due to the contraction of the muscle is shown and generally designated as 60. As seen in FIG. 6, the components of system 60 comprise therapeutic agent delivery implant 10, which includes rod 11 and patch 12; and a catheter 61, having an internal lumen and a mechanical system, generally designated as 62, to apply a force upon rod 11 sufficient to insert rod 11 into muscle 64. The mechanical system 62 may include a pushrod 63 as shown in FIG. 6. Pushrod 63 slidably translates along the longitudinal length of catheter 61.

One skilled in the art will appreciate that pushrod 63 is exemplary and that mechanical system 62 may include alternate mechanical systems that can include an actuator, spring, or hydraulic power. For example, pumping action by a fluid pump can cause a bio-compatible non-compressible fluid from the fluid source to be pumped from the proximal end of catheter 61 along the internal lumen of catheter 61, thereby urging therapeutic agent delivery implant 10 into muscle 64. Fluid source may be a non-toxic fluid source, such as contrast solutions used in ultrasound, fluoroscopy, and MRI procedures, or various brine solutions, to ensure that no toxic fluids, such as some therapeutic fluids, are washed into the bloodstream. Fluid pump may be a syringe or any other pumping means that can apply a pressure on the fluid. These alternative means could include a micro-pump and a collapsible bladder.

In the operation of the system of FIG. 6, catheter 61 is first positioned at the treatment site of the muscle. Catheter 61 may be introduced surgically or thoracoscopically to a treatment site at the epicardial surface of the heart, or may be introduced interventionally to a treatment site at the endocardial suface of the heart. One skilled in the art would appreciate that a thorascope or endoscope may be used instead of a catheter for non-interventional surgical procedures. Thus, at least a catheter, thorascope or endoscope may be used as means for delivering an implant to tissue (such as heart tissue) as described above and in the preceding paragraphs. The catheter, thorascope or endoscope may employ a mechanical system, such as a pushrod, actuator, spring or hydraulic power, to assist in delivering the implant to tissue, as described in this disclosure. FIG. 6 shows pushrod 63 in a first extended position with therapeutic agent delivery implant 10 contained within the internal lumen of catheter 61. The patch 12 of therapeutic agent delivery implant 10 is folded inside the internal lumen as catheter 61 is advanced to the target area for delivery of therapeutic agents to the diseased muscle. Patch 12 should be flexible enough such that the patch may stored in the catheter for delivery.

Referring to FIG. 7, delivery of therapeutic agent is initiated by applying a force upon therapeutic agent delivery implant 10, thereby urging rod 11 of therapeutic agent delivery implant 10 into muscle 64. As shown in FIG. 7, system 60 illustrates pushrod 63 in a second compressed position to insert rod 11 into muscle 64. The patch 12 is then secured to the surface of the muscle. One skilled in the art would appreciate that the patch can be stabilized to the surface by stapling, sewing, or bonding the patch to the muscle. A skilled artisan would appreciate that stapling, sewing, or otherwise mechanically attaching the patch to the muscle can be accomplished by introducing a stapling head or sewing head to the treatment site through the catheter as demonstrated in the pertinent art. The stapler or sewing apparatus may also be attached to the distal end of the catheter 61. Alternatively, attaching the patch to the muscle surface can be accomplished by bonding or adhesive methods, or by mounting a barb to the patch 12 for attaching the patch to the muscle.

Figure 8:
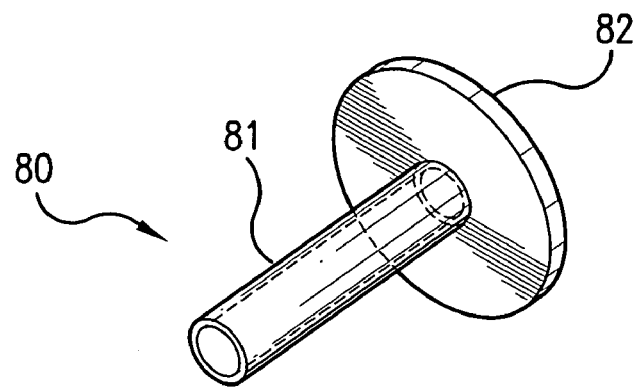
FIG. 8 is a perspective view of an alternative embodiment of the present invention.

In FIG. 8, a perspective view of an alternative embodiment of the present invention is illustrated and generally designated as system 80. The components of system 80 include rod 81 and patch 82. Rod 81 is substantially hollow. Hollow rods permit refilling rod 81 with therapeutic agents while the rod remains inserted into the muscle. Thus, treatment of the diseased muscle may continue without inserting another therapeutic delivery implant. Also, rods constructed from hollow fibers or wires can control therapeutic agent release or encapsulate cells. Rods constructed from hollow fiber membranes can contain living cells. Hollow metallic wire 81 permits therapeutic agent delivery from any site on the wire that a hole or porous membrane has been constructed. Further, a hollow wire or rod can be packed with therapeutic agent and excipients to enhance the therapeutic agent release. The hollow wire or rod can also be coated with therapeutic agent, a drug-containing polymer coating, and excipients.

Figure 9:
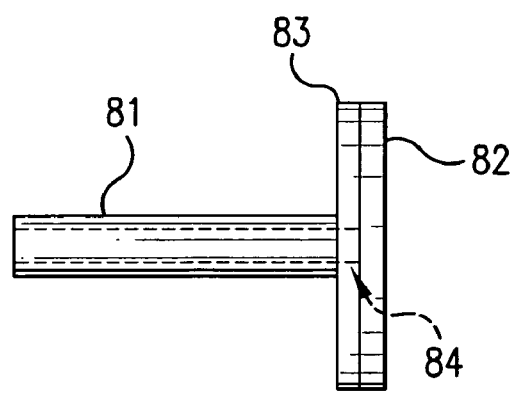
FIG. 9 is a side view of the embodiment of FIG. 8.

FIG. 9, a side view of the embodiment of FIG. 8, shows septum 83, adjacent patch 82 and hollow rod 81. Septum 83 allows needle access to hollow rod 81 so that the rod 81 can be refilled by pericardial access of a syringe containing therapeutic agents (not shown) on the epicardial side of the heart or the endocardial side of the heart. The syringe is inserted through septum 83 to access hollow rod 81. Septum 83 shown in FIG. 9 is exemplary. One skilled in the art would appreciate that a variety of access port 84 configurations can be designed to accommodate refilling hollow rod 81. For example, miniaturized versions of vascular access ports could be designed into the patch to allow refilling. A needleless access port may be placed on patch 82 wherein refilling with therapeutic agents may be accomplished by opening a valve on the access port. A person skilled in the art would appreciate that a variety of valves can be designed in any manner well known in the pertinent art, such as by utilizing a stopcock valve or by other mechanical valve means. Further, multiple rods may be attached to one patch, wherein the plurality of hollow rods can be connected to one central access port in a patch.

Figure 10:
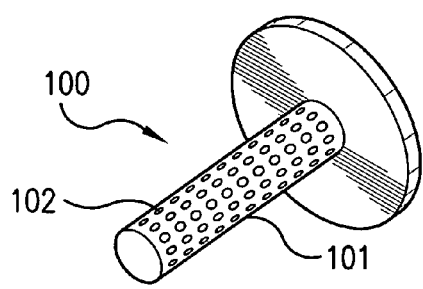
FIG. 10 is a perspective view of another alternative embodiment of the present invention illustrating orifices along the length of the rod for delivery of the therapeutic agent into the muscle of the patient.

FIG. 10 shows a perspective view of another alternative embodiment 100 of the present invention illustrating a plurality of orifices 102 along the longitudinal length of rod 101 for delivery of the therapeutic agent into the muscle of the patient. If the orifices 102 are small enough, osmotic pressure may be created in rod 101, and each pore can act as a mini osmotic pump. While the illustrated embodiment of implant 100 in FIG. 10 discloses rows of orifices 102 as being evenly sized and uniformly spaced along the circumference, these orifices 102 may be of different sizes or different shapes and may be located at different spacings along the rod 101. In this exemplary embodiment, however, these orifices will be evenly spaced along the rod to facilitate the even distribution of therapeutic drug into muscle.

Figure 11:
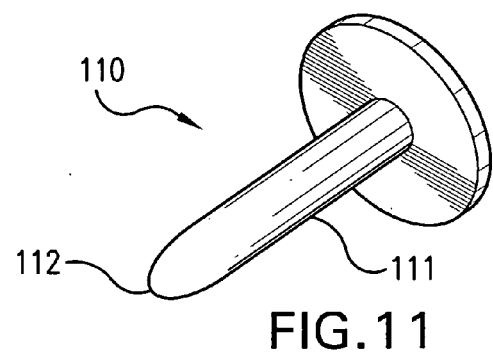
FIG. 11 is a perspective view of another alternative embodiment of the present invention illustrating an alternative configuration for the second end of the rod for insertion into the muscle of the patient.
Figure 12:
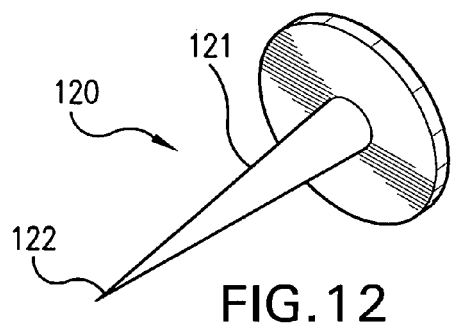
FIG. 12 is a perspective view of another alternative embodiment of the present invention illustrating another alternative configuration for the second end of the rod for insertion into the muscle of the patient.
Figure 13:
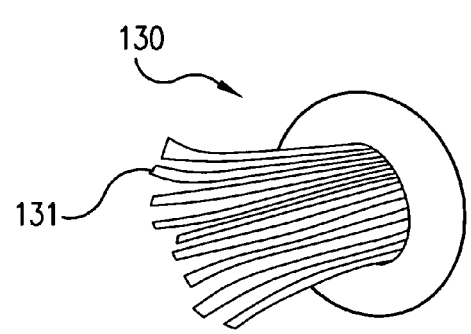
FIG. 13 is a perspective view of another alternative embodiment of the present invention showing a plurality of rods.

FIG. 11 is a perspective view of another alternative embodiment 110 of the present invention illustrating the second end 112 of rod 111. A skilled artisan would also appreciate that using a spherical or similarly round second end 112 minimizes trauma on the muscle and eases insertion into the muscle of the patient. The rod 111 may be conical in shape, substantially cylindrical in shape, or formed with a substantially conical tip. FIG. 12 is a perspective view of another alternative embodiment 120 of the present invention illustrating the second end 122 of rod 121. Second end 122 is substantially conical in shape. FIG. 13 is a perspective view of another alternative embodiment, generally designed at 130, of the present invention. Implant 130 has a plurality of rods 131 for therapeutic agent delivery.

In the operation of an alternate embodiment of the system of the present invention, a catheter (not shown) is first positioned at the treatment site of the muscle. The catheter has at least one internal lumen. The catheter may be introduced surgically or thoracoscopically to a treatment site at the epicardial surface of the heart, or may be introduced interventionally to a treatment site at the endocardial suface of the heart. The catheter includes a needle that slidably translates along the longitudinal length of the catheter. The needle has an internal lumen that is in fluid communication with a source of therapeutic drugs. Once positioned at the treatment site, the needle is extended beyond the distal end of the catheter by mechanical means into the muscle. Therapeutic agents are then injected into the muscle. One skilled in the pertinent art would appreciate that a variety of injection devices are referenced in the pertinent art. The needle is then withdrawn into the distal end of the catheter. A patch is then introduced through the distal end of the catheter and positioned at the treatment site of the muscle. The patch can be introduced to the muscle through a second internal lumen of the catheter or through a second catheter. The patch is then secured to the surface of the muscle. One skilled in the art would appreciate that the patch can be stabilized to the surface by the variety of methods discussed above.

In another alternate embodiment of the system of the present invention, the rod 11 and patch 12 may be constructed from shape memory material. Shape memory material returns an object to its original shape once heat is applied. Thus, rod 11 and patch 12 can be formed originally in a curved configuration (not shown) and constructed from shape memory material. The rod 11 and patch 12 can then be changed to a substantially straight configuration for insertion into the muscle. Once embedded into the muscle, body heat or an external source of heat can be applied to change the shape of the rod 11 and patch 12 back to its original curved shape. Accordingly, the curved shape permits the rod 11 and patch 12 to remain in the muscle upon contraction. Thus, a curved shape resulting from shape memory material may be used as means for (fixedly) attaching the patch onto tissue (such as heart tissue) to secure the rod within the tissue as described herein.

The term "therapeutic agent" as used throughout includes one or more "therapeutic drugs" or "genetic material." The term "therapeutic agent" used herein includes pharmaceutically active compounds, nucleic acids with and without carrier vectors such as lipids, compacting agents (such as histones), virus (such as adenovirus, adenoassociated virus, retrovirus, lentivirus and α-virus), polymers, hyaluronic acid, proteins, cells and the like, with or without targeting sequences. The therapeutics administered in accordance with the invention includes the therapeutic agent(s) and solutions thereof.

Specific examples of therapeutic agents used in conjunction with the present invention include, for example, pharmaceutically active compounds, proteins, cells, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic / antiproliferative / anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as linsidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warfarin sodium, Dicumarol, aspirin, prostaglandin inhibitors, platelet inhibitors and tick anti-platelet factors; vascular cell growth promotors such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the injection site. The delivery mediated is formulated as needed to maintain cell function and viability. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins that can be injected, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor $\alpha$ and $\beta$, platelet-derived endothelial growth factor, platelet-derived growth factor, tumor necrosis factor $\alpha$, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

The therapeutic delivery catheter may be used, for example, in any application for treating, preventing, or otherwise affecting the course of a disease or tissue or organ dysfunction. For example, the methods of the invention can be used to induce or inhibit angiogenesis, as desired, to prevent or treat restenosis, to treat a cardiomyopathy or other dysfunction of the heart, for treating Parkinson's disease or a stroke or other dysfunction of the brain, for treating cystic fibrosis or other dysfunction of the lung, for treating or inhibiting malignant cell proliferation, for treating any malignancy, and for inducing nerve, blood vessel or tissue regeneration in a particular tissue or organ.

One of skill in the art will realize that the examples described and illustrated herein are merely illustrative, as numerous other embodiments may be implemented without departing from the spirit and scope of the present invention.

What is claimed is:

1. A system for delivering a therapeutic agent into heart tissue comprising:
    at least one therapeutic agent delivery implant, wherein the implant comprises
        at least one rod carrying the therapeutic agent,
            the rod having a first end and second end,
            the rod adapted for insertion into heart tissue;
        a patch attached to one of said first and second ends of the rod, and having an inner surface adapted to fixedly attach the patch onto heart tissue to secure the rod within the heart tissue;
    a means for fixedly attaching the patch onto heart tissue to secure the rod within the heart tissue; and
    a means for delivering the implant to the heart tissue.

2. The system of claim 1 wherein the patch is integral with the rod.

3. The system of claim 1 wherein the patch is mounted to the rod.

4. The system of claim 1 wherein the means for fixedly attaching the patch onto heart tissue comprises a barb mounted on the inner surface of the patch for adjoining the patch onto tissue.

5. The system of claim 1 wherein the means for fixedly attaching the patch onto heart tissue comprises an adhesive applied to the inner surface of the patch for adjoining the patch onto heart tissue.

6. The system of claim 1 wherein the patch contains a therapeutic agent.

7. The system of claim 1 wherein the rod is substantially hollow.

8. The system of claim 1 wherein the rod further comprises at least one orifice to communicate with the heart tissue.

9. The system of claim 1 wherein the rod is substantially biodegradable.

10. The system of claim 1 wherein the rod is substantially porous.

11. The system of claim 1 wherein the rod further comprises a hollow metallic wire carrying the therapeutic agent.

12. The system of claim 7 wherein the patch further comprises an access port for refilling the rod with a therapeutic agent, wherein the access port is in fluid communication with the rod.

13. The system of claim 1 wherein the patch is substantially biodegradable.

14. The system of claim 1 wherein the rod is a shape-memory material.

15. The system of claim 1 wherein the patch is a shape-memory material.

16. The system of claim 1 wherein the patch is substantially flat.

17. A system for treating heart tissue with a therapeutic agent comprising:
    at least one therapeutic agent delivery implant,
    a catheter for delivering the implant to heart tissue, wherein
        the therapeutic agent delivery implant comprises at least one rod for carrying the therapeutic agent, the rod having a first end and a second end, and a patch having an inner surface adapted to fixedly attach the patch onto tissue to secure the rod within the tissue, the patch attached to one of said first and second ends of the rod, and
        the catheter comprises a proximal end, a distal end, and at least one internal lumen; and
    a means for attaching the patch onto heart tissue to secure the rod within the heart tissue.

18. The system of claim 17 wherein the means for attaching the patch to tissue comprises a stapler.

19. The system of claim 17 wherein the means for attaching the patch to tissue comprises a sewing apparatus.

20. The system of claim 17 wherein the means for attaching the patch to tissue comprises a barb mounted on the inner surface of the patch for adjoining the patch onto tissue.

21. The system of claim 17 wherein the means for attaching the patch to tissue comprises an adhesive applied to the inner surface of the patch for adjoining the patch onto tissue.

* * * * *

UNITED STATES PATENT AND TRADEMARK OFFICE
CERTIFICATE OF CORRECTION

PATENT NO. : 7,108,685 B2
APPLICATION NO. : 10/121618
DATED : September 19, 2006
INVENTOR(S) : Helmus Page 1 of 1

It is certified that error appears in the above-identified patent and that said Letters Patent is hereby corrected as shown below:

Column 1, line 14, "modem practice" should read -- modern practice --.

Signed and Sealed this

Fifteenth Day of April, 2008

JON W. DUDAS
*Director of the United States Patent and Trademark Office*